(12) United States Patent
Baumfalk et al.

(10) Patent No.: US 7,360,400 B2
(45) Date of Patent: Apr. 22, 2008

(54) DEVICE, METHOD AND COMPUTER PROGRAMME PRODUCT FOR CARRYING OUT INTEGRITY TESTS ON FILTER ELEMENTS

(75) Inventors: Reinhard Baumfalk, Göttingen (DE); Maik Jornitz, Bellport, NY (US); Ralf Lausch, Göttingen (DE); Christian Oldendorf, Göttingen (DE); Oscar-Werner Reif, Hannover (DE)

(73) Assignee: Sartorius Biotech GmbH, Goettingen (DE)

( * ) Notice: Subject to any disclaimer, the term of this patent is extended or adjusted under 35 U.S.C. 154(b) by 119 days.

(21) Appl. No.: 11/446,789

(22) Filed: Jun. 5, 2006

(65) Prior Publication Data

US 2006/0218991 A1    Oct. 5, 2006

Related U.S. Application Data

(63) Continuation of application No. 10/492,263, filed as application No. PCT/EP02/11451 on Oct. 14, 2002.

(30) Foreign Application Priority Data

Oct. 17, 2001    (DE) .............................. 101 51 271

(51) Int. Cl.
G01N 15/08    (2006.01)

(52) U.S. Cl. ........................................................ 73/38

(58) Field of Classification Search ................... 73/38; 210/85; 96/417; 702/50, 182
See application file for complete search history.

(56) References Cited

U.S. PATENT DOCUMENTS

| | | | |
|---|---|---|---|
| 4,435,713 A | 3/1984 | Gasparaitis et al. |
| 4,685,066 A | 8/1987 | Hafele et al. |
| 4,701,861 A | 10/1987 | Kauke |
| 5,192,424 A | 3/1993 | Beyne et al. |
| 5,236,477 A | 8/1993 | Koketsu |
| 5,524,284 A | 6/1996 | Marcou et al. |
| 5,563,334 A | 10/1996 | Bracht et al. |

(Continued)

FOREIGN PATENT DOCUMENTS

DE    201 04 481 U 1    7/2001

(Continued)

*Primary Examiner*—Hezron Williams
*Assistant Examiner*—John Fitzgerald
(74) *Attorney, Agent, or Firm*—Anthony J. Casella; Gerald E. Hespos

(57) ABSTRACT

The invention relates to a device for carrying out integrity tests on filter elements by means of test gases, comprising a device housing (3), with an electronic controller (4), arranged therein for regulation and control of the progress of a test programme for filter elements, a filter housing (6), for housing a filter element (2) under test, a pneumatic unit (5), connected to the controller (4) and the filter housing (6), in particular for the generation and measurement of gas pressures, an electronic memory unit (10), which may be connected to the filter element (2) under test and a communication unit (13'), connected to the controller (4), for the exchange of data between the controller (4) and the electronic memory element (10). The communication unit (13') is preferably embodied as an antenna (14') and the electronic memory element (10) as a transponder (11). In addition to the device a method for carrying out integrity tests and a computer programme product are also disclosed.

15 Claims, 3 Drawing Sheets

U.S. PATENT DOCUMENTS

Figure 1:
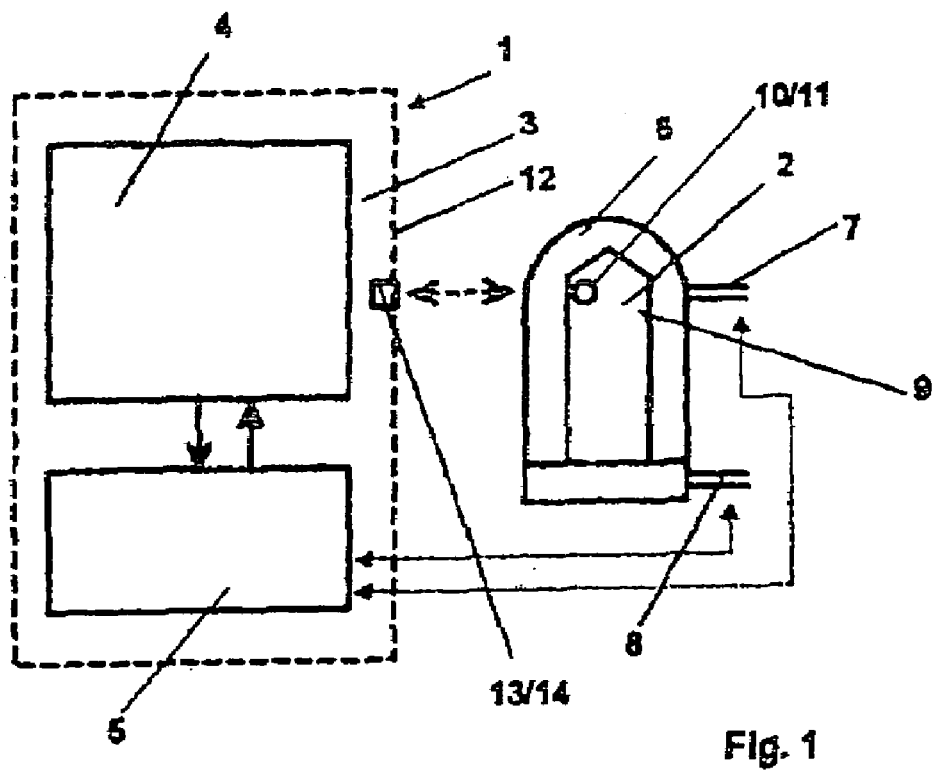

| | | |
|---|---|---|
| 5,594,161 A | 1/1997 | Randhahn et al. |
| 5,616,828 A | 4/1997 | Kuczenski |
| 5,674,381 A | 10/1997 | Den Dekker |
| 5,674,404 A * | 10/1997 | Kenley et al. ............... 210/741 |
| 6,040,777 A * | 3/2000 | Ammann et al. ........... 340/632 |
| 6,186,140 B1 | 2/2001 | Hoague |
| 6,334,959 B1 * | 1/2002 | Sutton et al. ............... 210/767 |
| 6,391,102 B1 | 5/2002 | Bodden et al. |
| 6,537,444 B2 | 3/2003 | Wilberscheid et al. |
| 6,551,503 B2 | 4/2003 | Niers et al. |
| 6,558,444 B1 | 5/2003 | Hunter |
| 6,711,524 B2 | 3/2004 | Wolf et al. |

FOREIGN PATENT DOCUMENTS

| | | |
|---|---|---|
| DE | 101 51 271 A1 | 5/2003 |
| GB | 2303082 A | 2/1997 |
| JP | 07275621 A | 10/1995 |
| WO | WO 94/22551 A1 | 10/1994 |
| WO | WO 97/26563 A1 | 7/1997 |
| WO | WO 00/32298 | 6/2000 |
| WO | WO 00/40322 | 7/2000 |
| WO | WO 2004/085027 A1 | 10/2004 |

* cited by examiner

DEVICE, METHOD AND COMPUTER PROGRAMME PRODUCT FOR CARRYING OUT INTEGRITY TESTS ON FILTER ELEMENTS

CROSS REFERENCE TO RELATED APPLICATIONS

This application is a continuation application of U.S. patent application Ser. No. 10/492,263 filed Apr. 7, 2004 which is a 371 of PCT/EP02/11451 filed Oct. 14, 2002.

DESCRIPTION

The invention relates to an apparatus for carrying out an integrity test on filter elements by means of test gases, essentially comprising an electronic control unit or closed-loop and/or open-loop control of the test program procedure for the filter elements which are to be tested and are arranged in a filter housing, and a pneumatic unit which is connected to the control unit and to the filter housing, in particular for provision and measurement of gas pressures.

The invention also relates to a method for carrying out an integrity test on filter elements by means of a test apparatus.

The invention likewise relates to a computer program product for carrying out integrity tests on filter elements.

Apparatuses for carrying out integrity tests on filter elements are described, for example, in DE 39 17 856 C2, DE 199 26 002 A1, and DE 43 39 589 C2.

These known apparatuses have the disadvantage that at least data which characterizes the filter elements to be tested must be manually entered in the test apparatus in order to make it possible in this way to carry out the integrity tests which are specified for these filter elements, such as a pressure maintenance test, diffusion test, bubble point test, or water intrusion test. This results in considerable potential errors caused by operators incorrectly associating test data with the filter elements. One object of the invention is therefore to propose an apparatus for carrying out integrity tests on filter elements, which largely precludes manual errors by the operator.

In conjunction with the precharacterizing clause of claim 1, this object is achieved in that the control unit is connected to a communication part which is adjacent to the filter elements to be tested, and via which data can be interchanged between the control unit and electronic memory elements which are arranged on the filter elements.

Since the control unit can interchange data via its communication part with electronic memory elements which are arranged on the filter elements, this makes it possible for the test apparatus or its control unit to automatically read the individual data items which characterize the filter elements to be tested. Potential errors which resulting from incorrect association of tested data with filter elements are thus reliably avoided.

According to one preferred embodiment of the invention, the communication part is an antenna for transmitting and receiving radio-frequency signals, and the electronic memory element is a transponder arranged on the filter element. The communication part preferably comprises a data interface, a processor unit and an antenna.

Transponders can be read and, when required, written to without any contact, with no visual contact being required to the read/write station or the antenna of the controller. User-defined data may in this case be stored without any problems on the microchip of the transponder. In addition, transponder data can be protected by means of a password.

According to a further preferred embodiment of the invention, the antenna is sheathed by an electrically poorly conductive material which comprises a chemically and thermally stable organic polymer.

The use of a poorly conductive material on the one hand does not significantly influence the performance of the antenna and, on the other hand, the organic polymer protects the antenna.

According to a further preferred embodiment of the invention, the antenna is a component of a housing wall of an apparatus housing or is at least arranged adjacent to the housing wall, with the housing wall being formed from an electrically poorly conductive material at least in an area adjacent to the antenna.

If the antenna is arranged within the apparatus housing, that is to say outside the filter housing, there is no need for the antenna to have its own sheathing since it is protected by the apparatus housing. However, for the antenna performance, it is advantageous for the housing wall to be formed from an electrically poorly conductive material, at least in an area adjacent to the antenna. In order to improve the antenna performance, it is advantageous to arrange the antenna or that part of the housing wall to which the antenna is fitted such that the antenna points at the transponders or filter elements, at least for communication.

According to one preferred embodiment of the invention, the antenna is arranged outside the apparatus housing in the filter housing, and is connected to the control unit via an electrical line.

Arranging the antenna in the filter element ensures reliable transmission with low power levels. Good access is therefore provided to the filter element data even in the installed state, and it is simple to check and identify the filter cartridge or the filter element at any time. According to a further preferred embodiment of the invention, a pressure maintenance test, a diffusion test, a bubble point test and/or a water intrusion test can be carried out as the integrity test. This means that all the important integrity tests can be carried out using the apparatus according to the invention. Further tests may also be added, if required.

According to a further preferred embodiment of the invention, the data interchange between the control unit and the electronic memory elements of the filter elements comprises the reading of data from the electronic memory elements to the control unit and/or the reading of data to the electronic memory elements from the control device and/or the overwriting of data in the electronic memory elements by the control unit. The reading to and storage of data in the electronic memory elements and transponders makes it possible in particular to store test results (test record file) on the transponder chip by means of a writing process. This makes it possible to produce a documentation-relevant "electronic accompanying paper". Particularly if the integrity system is used at different locations and a permanent data backup on a central data management computer is not always provided, this always ensures that all the necessary documents are available at the location of the filtration system—that is to say the point at which the filter element to be tested is used. In this case, it is possible to store not only the current test result but also the entire "history" in the memory of the transponder, for analysis purposes.

According to a further preferred embodiment of the invention, the data to be interchanged is identification data for the filter elements, limit values for test data, measured test data and/or limiting data. Limiting data may, in particular, include the life and maximum permissible regeneration or sterilization cycles for the filter elements.

The known methods have the disadvantages mentioned above.

A further object of the invention is therefore to propose a method for testing filter elements, which largely precludes manual errors by the operator while carrying out integrity tests.

This object is achieved in conjunction with the precharacterizing clause of claim 13, by carrying out the following steps:
a) identification data and/or limiting data and/or limit values for test data are/is read from electronic memory elements which are arranged on the respective filter elements,
b) the data from a) is stored in the test apparatus,
c) the integrity tests provided on the basis of the data are carried out.

The potential faults which can occur with manual data transfer are reliably avoided by reading data from electronic memory elements which are associated with the respective filter elements, and by storing the data in the test apparatus.

According to a further preferred embodiment of the invention, once the integrity tests have been carried out, a test is carried out in a further step to determine whether the limit values and/or the limiting data for at least one of the measured data items have or has been reached or exceeded. If the limit values and/or the limiting data have or has been reached or exceeded, the filter elements are then inhibited in a subsequent step.

The testing and, if necessary, subsequent inhibiting of the filter elements for further use considerably improves the reliability achieved by the integrity tests.

According to a further preferred embodiment of the invention, once the integrity tests have been carried out, the measured integrity data is written to the electronic memory elements or transponders for the respective filter elements.

Reliable "electronic accompanying papers" are thus produced by writing the measured integrity data of the electronic memory elements or transponders for the respective filter elements. This also allows the validity to be improved for future, further integrity tests.

A further object of the invention is to propose a computer program product for testing filter elements using the claimed test methods.

Since the assisting program parts can be called up from a program, this considerably simplifies the design of a corresponding test apparatus and the method.

According to one preferred embodiment of the invention program parts which assist the communication between a test apparatus and a transponder which is associated with the filter element to be tested can be called up from the program memory.

The program parts which assist communication allow and speed up the automatic communication between the test apparatus and the transponders for the filter elements.

Figure 2:
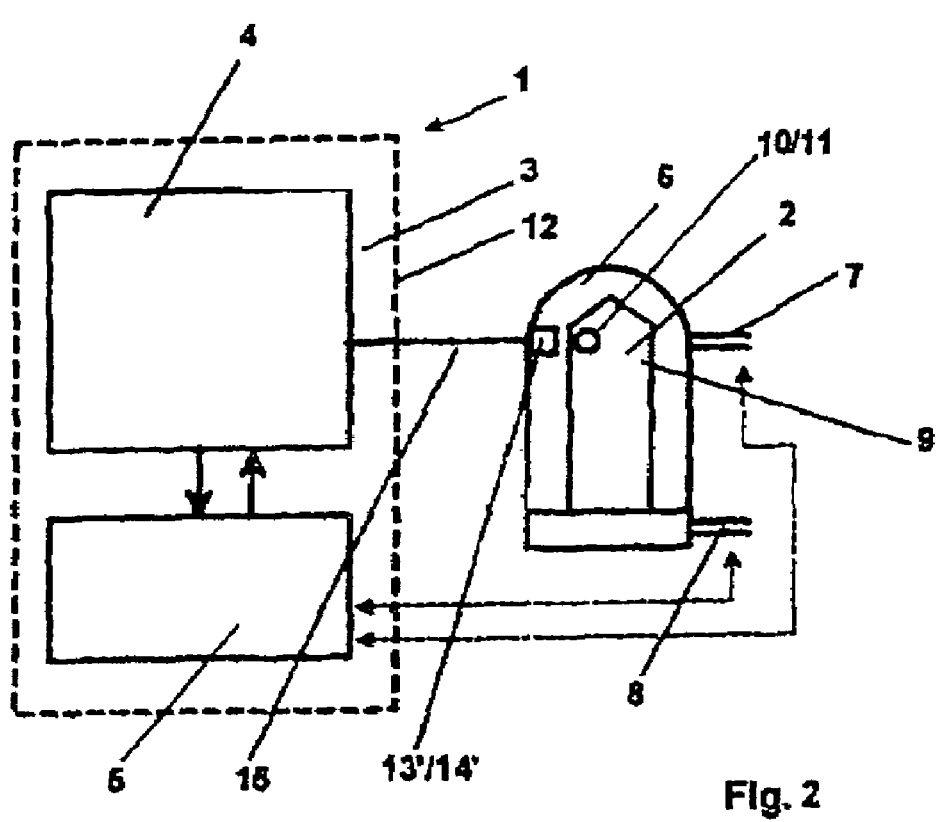
Figure 3:
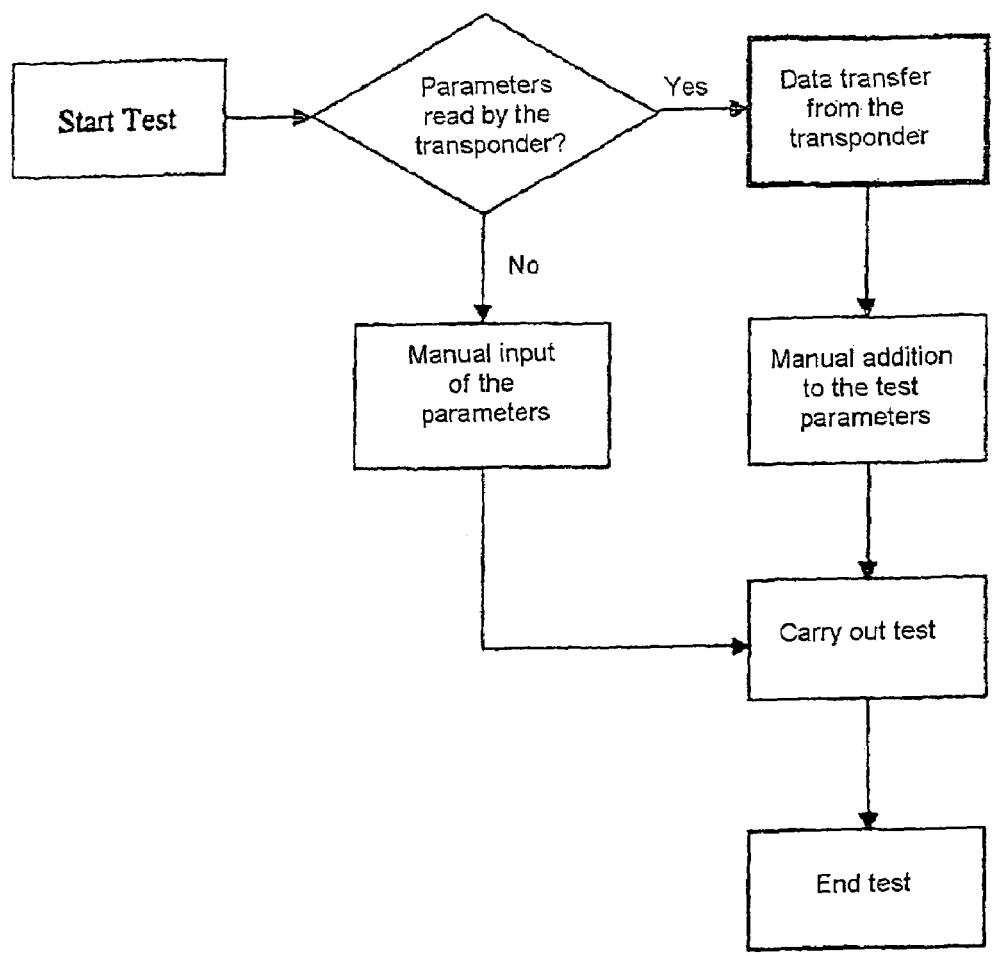
Figure 4:
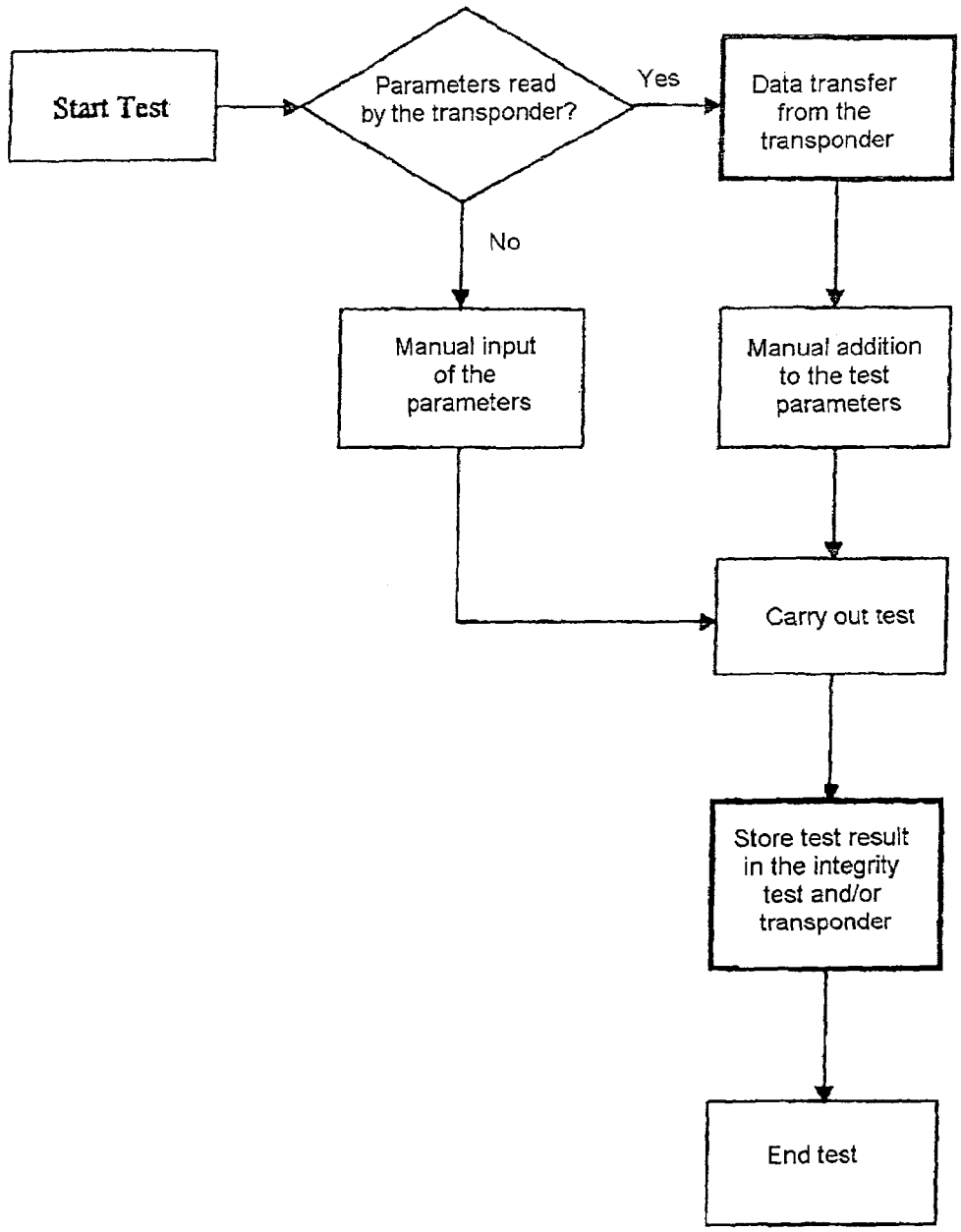

Further details of the invention will become evident from the following comprehensive description and the attached drawings, which illustrate the preferred exemplary embodiments of the invention, and in which:

FIG. 1 shows a schematic illustration of an apparatus for carrying out integrity tests on filter elements having a communication part which is arranged within an apparatus housing, FIG. 2 shows a schematic illustration of an apparatus for monitoring integrity tests on filter elements having an electronic communication part which is arranged in a filter housing, FIG. 3 shows a schematic illustration of a method procedure based on an algorithm, in which data is only read from a transponder, and FIG. 4 shows a schematic illustration of a method procedure based on an algorithm, in which both read access and write access are made to the transponder for a filter element.

An apparatus 1 or test apparatus for carrying out integrity tests on filter elements 2 essentially comprises an apparatus housing 3, and electronic control unit 4 and a pneumatic unit 5.

The filter elements 2 to be tested are arranged in a filter housing 6 which has an inlet line 7 and an outlet line 8.

The pneumatic unit 5 is provided with closed-loop or open-loop control by the control unit 4 and is used in particular in a known manner for production and measurement of gas pressures. Lines which are not illustrated together with sensors and actuators which are not illustrated are used in a known manner for monitoring and measurement of the integrity of the filter element 2.

At its upper end 9, the filter element 2 has an electronic memory element 10 in the form of a transponder 11. A communication part 13 is arranged on one housing wall 12 of the apparatus housing 3, and is in the form of an antenna 14.

According to another embodiment, the communication part 13' and the antenna 14' are arranged in the filter housing 6, and are connected to the control unit 4 via an electrical connection 15.

In order to carry out the method, identification data and/or limiting data and/or limit values for test data are/is read from the transponder 11 for the filter element 2 and are/is stored in a memory, which is not illustrated, for the control unit 4, which provides closed-loop or open-loop control for carrying out the integrity tests which are provided on the basis of the data. The control unit 4 checks whether at least one of the measured data items has reached or exceeded the limit values and/or the limiting data. If the limit values and/or the limiting data have or has been reached or exceeded, the control unit 4 inhibits the filter elements 2. The integrity data which is measured after carrying out the integrity test is written to the transponders 11 for the respective filter elements 2. The control unit 4 has program memories from which program parts which assist the process of carrying out the method can be called up.

FIG. 3 shows that the method procedure based on an algorithm, in which only data is read from the transponder. After starting the test method, test parameter data is transferred from the transponder 11. The test parameters in this case are:
 filter element number
 filter element type
 maximum diffusion
 test pressure diffusion
 bubble point limit value
 stabilization time
 test time The integrity tests are carried out once any manual addition to the test parameters has been included.

FIG. 4 shows the method procedure based on an algorithm in which the transponder 11 is accessed both for reading and writing. In this case, once the test has been carried out, the test result is stored in the control unit 4 and/or in the transponder 11. By way of example, the test result which is stored comprises:
 file name
 file size
 user name time and date
checksum
test assessment (positive/negative)
measured diffusion
test pressure setting
measured bubble point value
test parameters.

The invention claimed is:

1. An apparatus for carrying out an integrity test on filter elements by means of test gases, including an electronic control unit or closed-loop and/or open-loop control of the test program procedure for the filter elements which are to be tested and are arranged in a filter housing, and a pneumatic unit which is connected to the control unit and to the filter housing, in particular for provision and measurement of gas pressures, wherein the improvement is that the control unit is connected to a communication part which is adjacent to the filter elements to be tested, and via which data can be interchanged between the control unit and electronic memory elements which are arranged on the filter elements; wherein said integrity test parameters include at least the following: filter element number, filter element type, maximum diffusion, test pressure diffusion, bubble point limit value, stabilization time and test time; wherein said apparatus further comprises a means for carrying out a test to determine whether limit values and/or limiting data has been reached or exceeded by at least one measured test data item and a means for said control unit to electronically inhibit said filter elements from further use if said limit values and/or said limiting data has been reached or exceeded.

2. The apparatus as claimed in claim 1, wherein said electronic control unit is password protected.

3. The apparatus as claimed in claim 1, wherein the communication part comprises a data interface, a processing unit and an antenna.

4. The apparatus as claimed in claim 1, wherein a pressure maintenance test, a diffusion test, a bubble point test and/or a water intrusion test can be carried out as the integrity test.

5. The apparatus as claimed in claim 1, wherein the data interchanged between the control unit and the electronic memory elements of the filter elements comprises the reading of data from the electronic memory elements to the control unit and/or the reading of data to the electronic memory elements from the control device and/or the overwriting of data in the electronic memory elements by the control unit.

6. The apparatus as claimed in claim 5, wherein the data is identification data for the filter elements, limit values for test data, measured test data and/or limiting data.

7. The apparatus as claimed in claim 6, wherein the data is data which limits the life and maximum permissible regeneration or sterilization cycles of the filter elements.

8. The apparatus as claimed in claim 1, wherein the communication part is an antenna for transmitting and receiving radio-frequency signals, and the electronic memory element is a transponder.

9. The apparatus as claimed in claim 8, wherein the antenna is a component of a housing wall of an apparatus housing or is arranged adjacent to the housing wall, and in that the housing wall is formed from an electrically poorly conductive material at least in an area adjacent to the antenna.

10. The apparatus as claimed in claim 9, wherein the part of the housing wall which is adjacent to the antenna is arranged such that, at least for communication, it points at the transponders of the filter elements.

11. The apparatus as claimed in claim 8, wherein the antenna is arranged outside the apparatus housing and is connected to the control unit via an electrical line.

12. The apparatus as claimed in claim 11, wherein the antenna is arranged in the filter housing.

13. The apparatus as claimed in claim 8, wherein the antenna is sheathed by an electrically poorly conductive material.

14. The apparatus as claimed in claim 13, wherein the material which sheaths the antenna comprises a chemically and thermally stable organic polymer.

15. An apparatus for carrying out an integrity test on filter elements by means of test gases, including an electronic control unit or closed-loop and/or open-loop control of a test program procedure for the filter elements which are to be tested and are arranged in a filter housing, and a pneumatic unit which is connected to the control unit and to the filter housing, in particular for provision and measurement of gas pressures, wherein the improvement is that the control unit is connected to a communication part which is adjacent to the filter elements to be tested, and via which data can be interchanged between the control unit and electronic memory elements which are arranged on the filter elements, wherein said integrity test parameters include at least the following: filter element number, filter element type, maximum diffusion, test pressure diffusion, bubble point limit value, stabilization time and test time; wherein said apparatus further comprises a means for carrying out a test to determine whether limit values and/or limiting data has been reached or exceeded by at least one measured test data item and a means for said control unit to electronically inhibit said filter elements from further use if said limit values and/or said limiting data has been reached or exceeded.

* * * * *